(12) United States Patent
Kobayashi et al.

(10) Patent No.: US 10,281,429 B2
(45) Date of Patent: May 7, 2019

(54) SEMICONDUCTOR MICRO-ANALYSIS CHIP AND METHOD OF MANUFACTURING THE SAME

(71) Applicant: KABUSHIKI KAISHA TOSHIBA, Minato-ku, Tokyo (JP)

(72) Inventors: Kentaro Kobayashi, Tokyo (JP); Michihiko Nishigaki, Kawasaki Kanagawa (JP); Hiroshi Hamasaki, Hiratsuka Kanagawa (JP); Naofumi Nakamura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 128 days.

(21) Appl. No.: 15/408,677

(22) Filed: Jan. 18, 2017

(65) Prior Publication Data

US 2017/0122905 A1     May 4, 2017

Related U.S. Application Data

(63) Continuation of application No. PCT/JP2015/057607, filed on Mar. 10, 2015.

(30) Foreign Application Priority Data

Jul. 18, 2014   (JP) .................................. 2014-147613

(51) Int. Cl.
*G01N 27/447*     (2006.01)
*G01N 15/10*      (2006.01)

(52) U.S. Cl.
CPC ... *G01N 27/44791* (2013.01); *G01N 15/1031* (2013.01); *G01N 15/1056* (2013.01); *G01N 2015/1006* (2013.01)

(58) Field of Classification Search
CPC ......... G01N 27/44791; G01N 27/3278; G01N 33/48721; G01N 15/1031; G01N 15/1056; G01N 2015/1006
See application file for complete search history.

(56) References Cited

U.S. PATENT DOCUMENTS

| 5,132,745 A | 7/1992 | Kwasnick et al. |
| 2004/0051154 A1 | 3/2004 | Yamakawa et al. |

(Continued)

FOREIGN PATENT DOCUMENTS

| JP | 2002277380 A | 9/2002 |
| JP | 2008039541 A | 2/2008 |

(Continued)

OTHER PUBLICATIONS

Machine Translation to English of JP 2008-216038 A (Year: 2008).*

(Continued)

*Primary Examiner* — J. Christopher Ball
(74) *Attorney, Agent, or Firm* — Holtz, Holtz & Volek PC

(57) ABSTRACT

According to one embodiment, a semiconductor microanalysis chip includes a first flow channel provided with a substrate surface, the flow channel engraved on the substrate into which a sample liquid can flow, micropore provided with a part of the flow channel, a reservoir provided with at least one end of the flow channel, the reservoir engraved on the substrate for inlet and outlet of the sample liquid, and a first electrode provided with a part of the flow channel or of the reservoir. The electrode is disposed from the bottom surface of the flow channel or of the reservoir to the substrate surface, and a side surface which connects the bottom surface and the substrate surface is tapered for reducing a bend in a height direction of the electrode.

15 Claims, 20 Drawing Sheets

(56) References Cited

U.S. PATENT DOCUMENTS

| | | |
|---|---|---|
| 2004/0144658 A1 | 7/2004 | Flory |
| 2008/0311375 A1 | 12/2008 | Harnack et al. |
| 2012/0292496 A1 | 11/2012 | Escobedo et al. |
| 2012/0298511 A1 | 11/2012 | Yamamoto |
| 2014/0231274 A1 | 8/2014 | Oki et al. |
| 2014/0252505 A1 | 9/2014 | Kobayashi et al. |
| 2014/0255911 A1 | 9/2014 | Hongo et al. |
| 2014/0256028 A1 | 9/2014 | Kobayashi et al. |
| 2014/0256031 A1 | 9/2014 | Kobayashi et al. |
| 2015/0041316 A1 | 2/2015 | Miki et al. |

FOREIGN PATENT DOCUMENTS

| | | |
|---|---|---|
| JP | 2008216038 A | 9/2008 |
| WO | 2013076943 A1 | 5/2013 |

OTHER PUBLICATIONS

Machine Translation to English of JP 2008-039541 A (Year: 2008).*
International Search Report (ISR) and Written Opinion dated May 19, 2015 issued in International Application No. PCT/JP2015/057607.

* cited by examiner

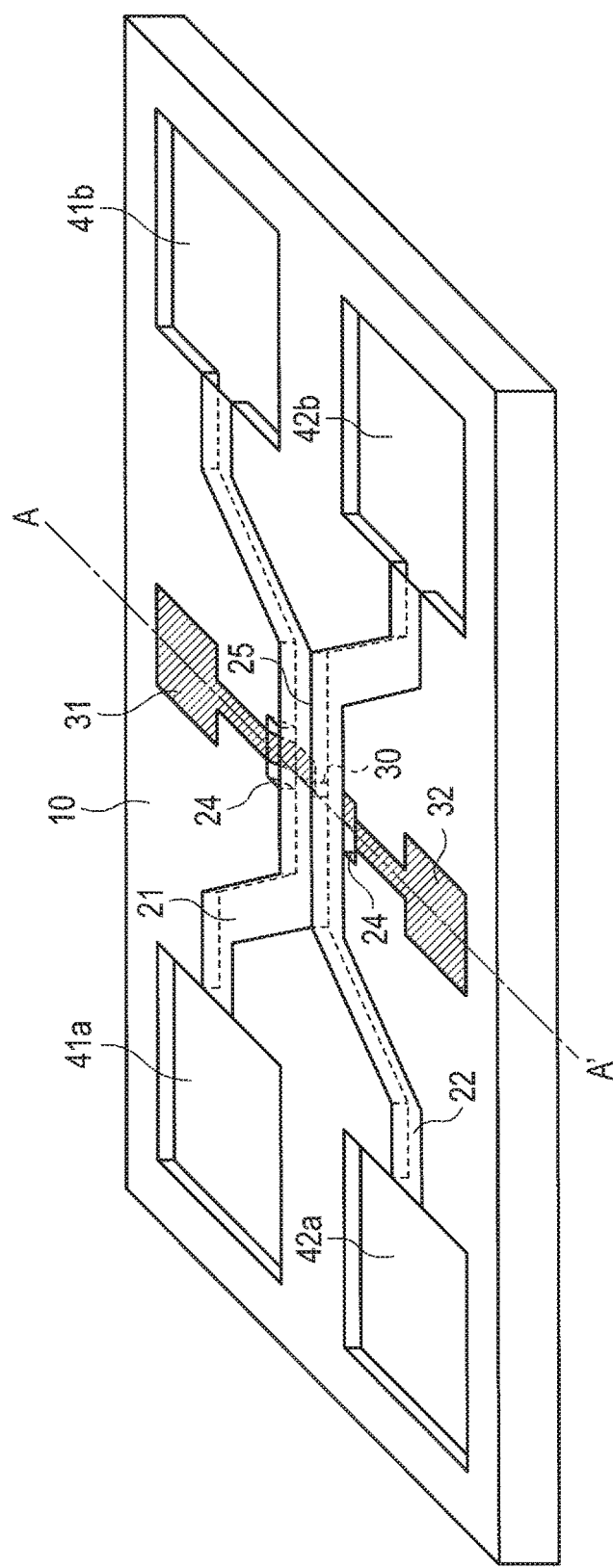
F I G. 1

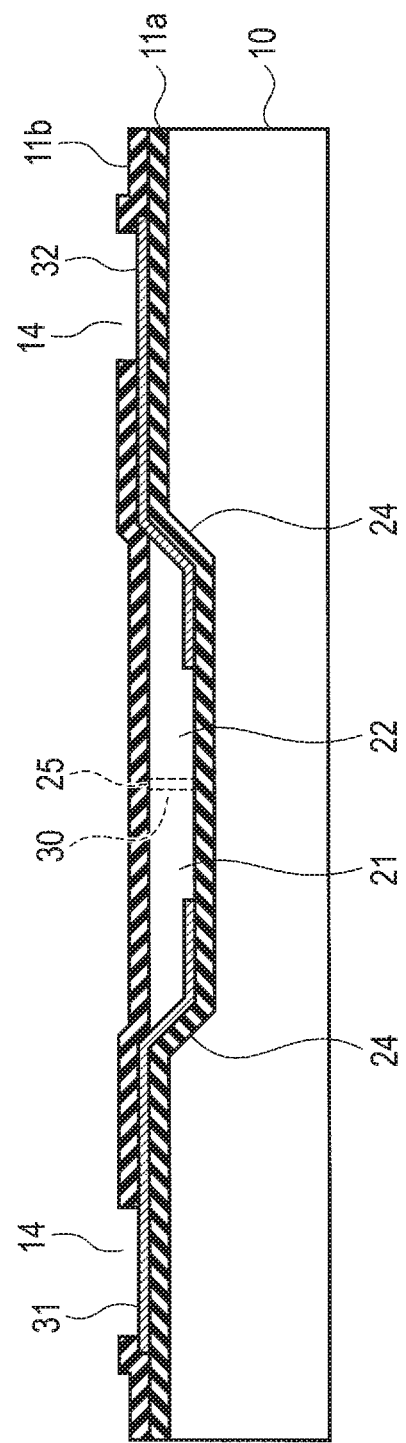
F I G. 2

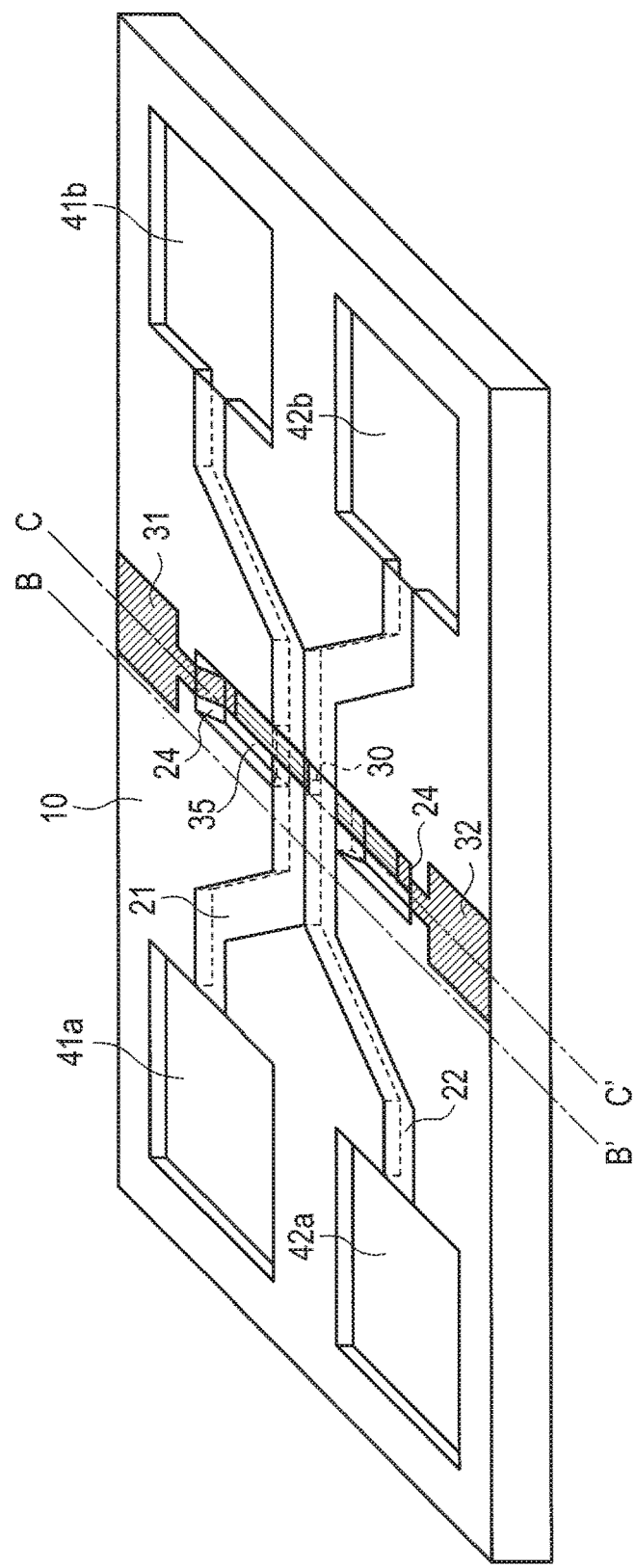
F I G. 4

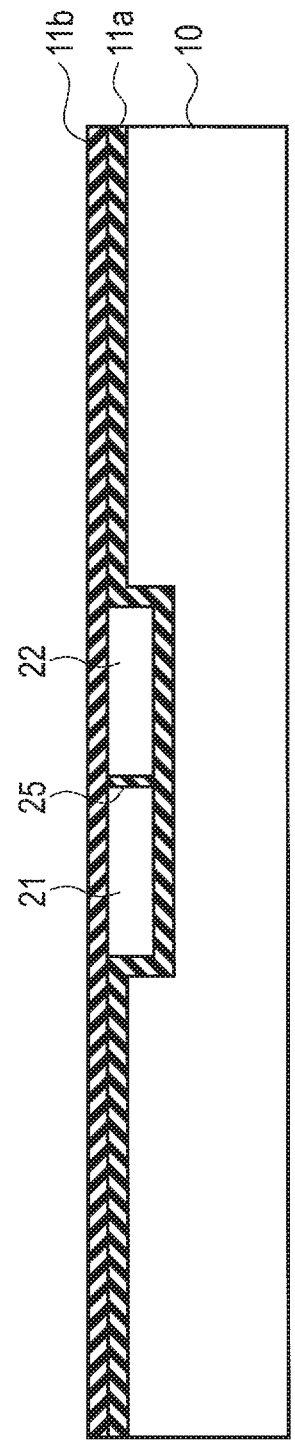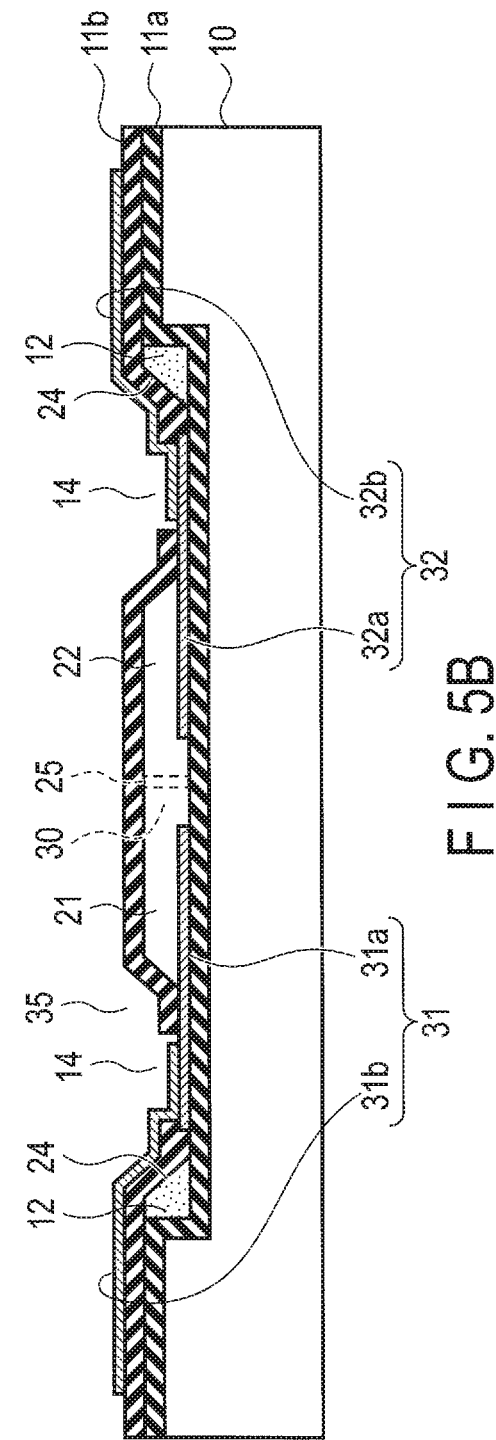

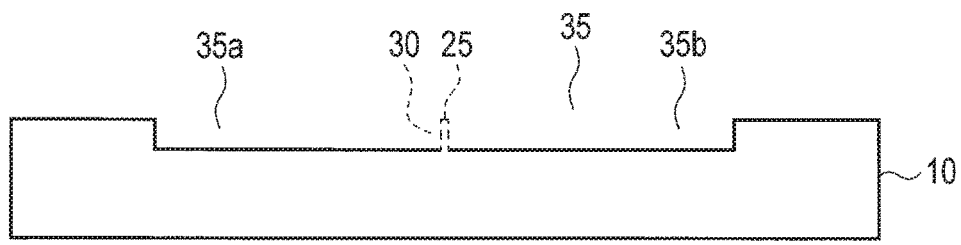
F I G. 6A
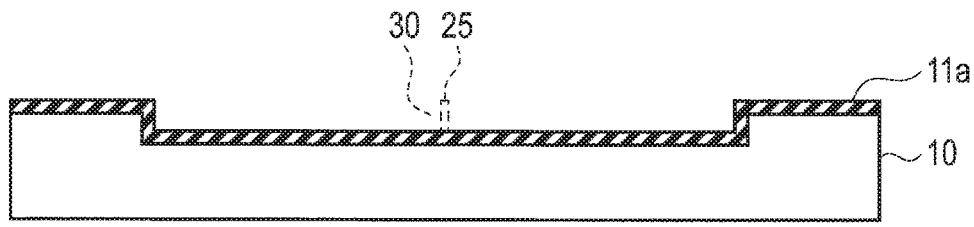
F I G. 6B
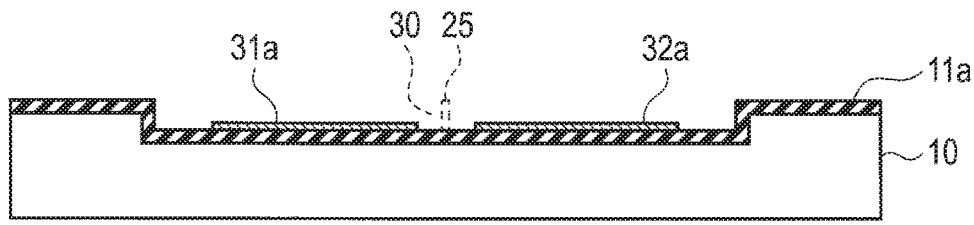
F I G. 6C
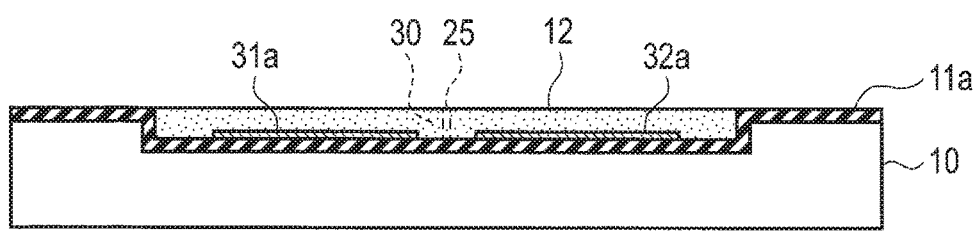
F I G. 6D

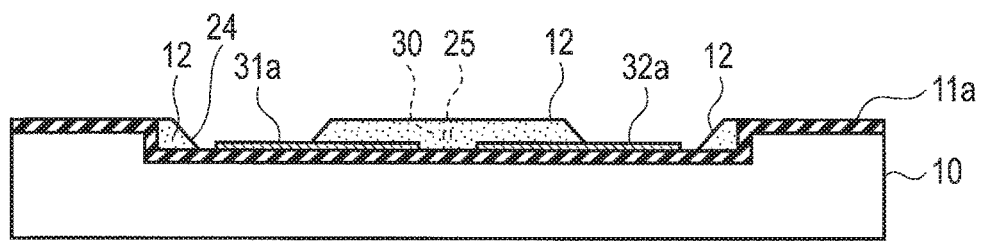
F I G. 6E
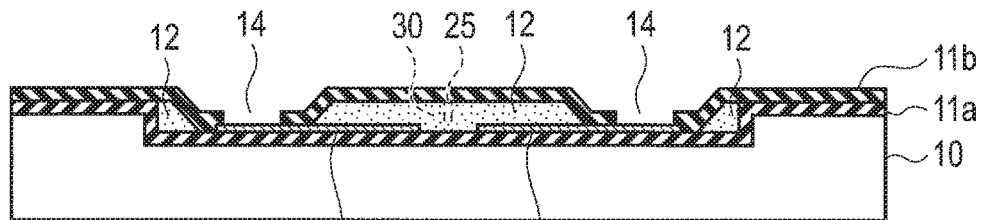
F I G. 6F
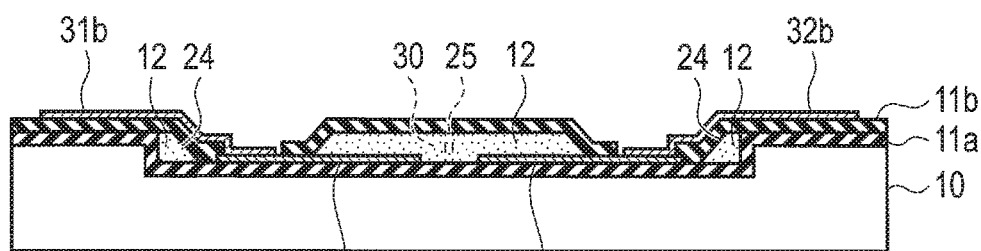
F I G. 6G

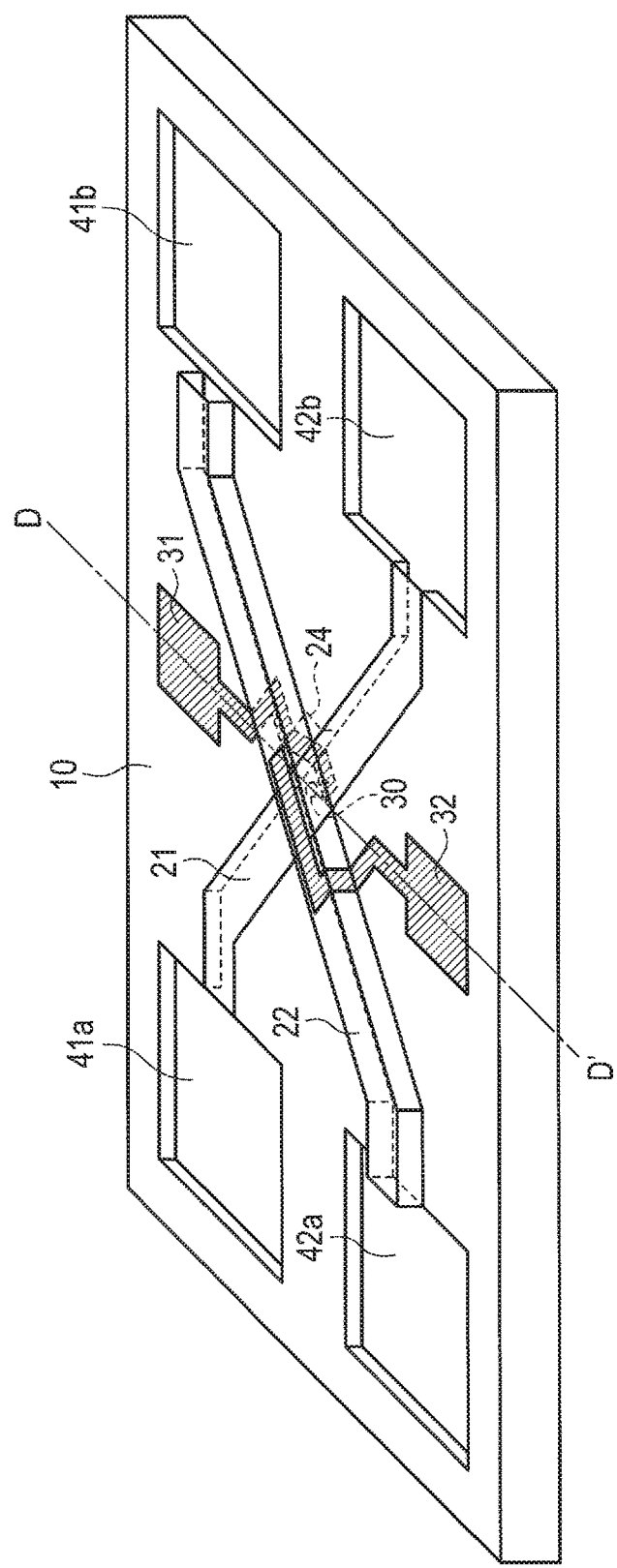
F I G. 7

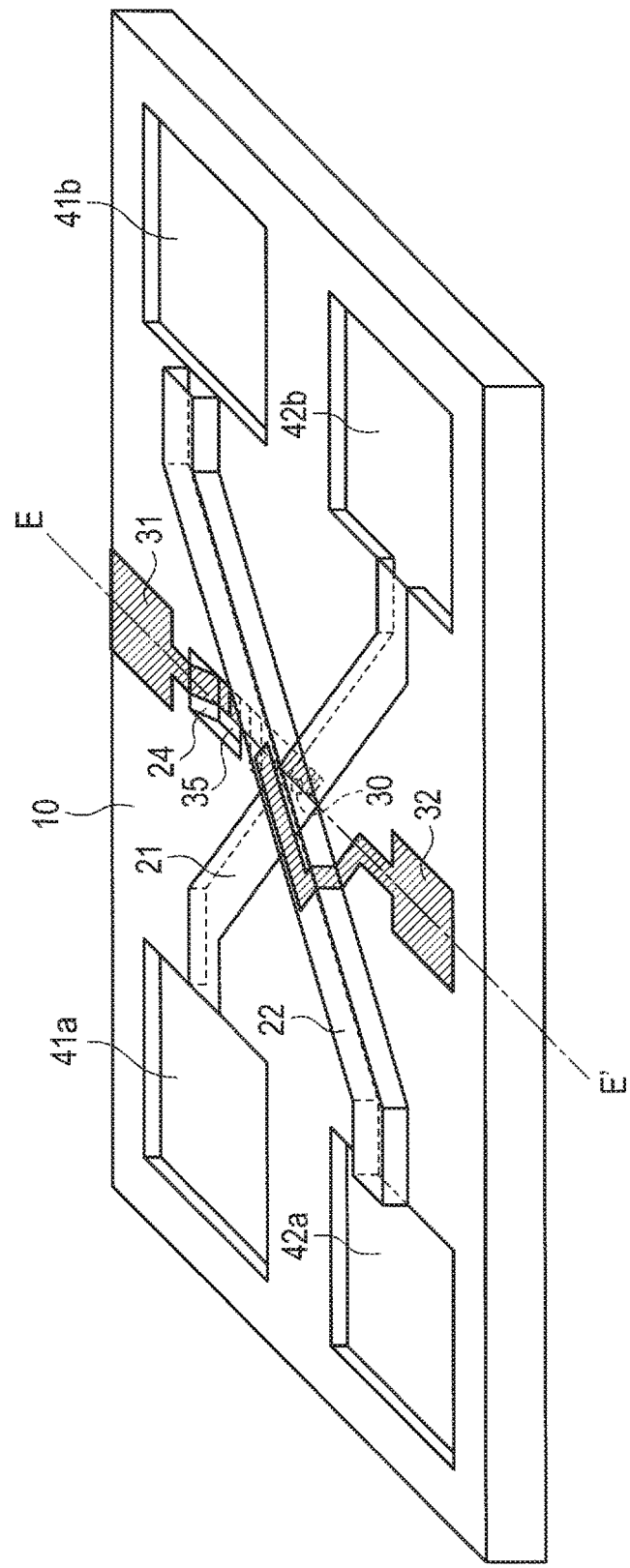
F I G. 9

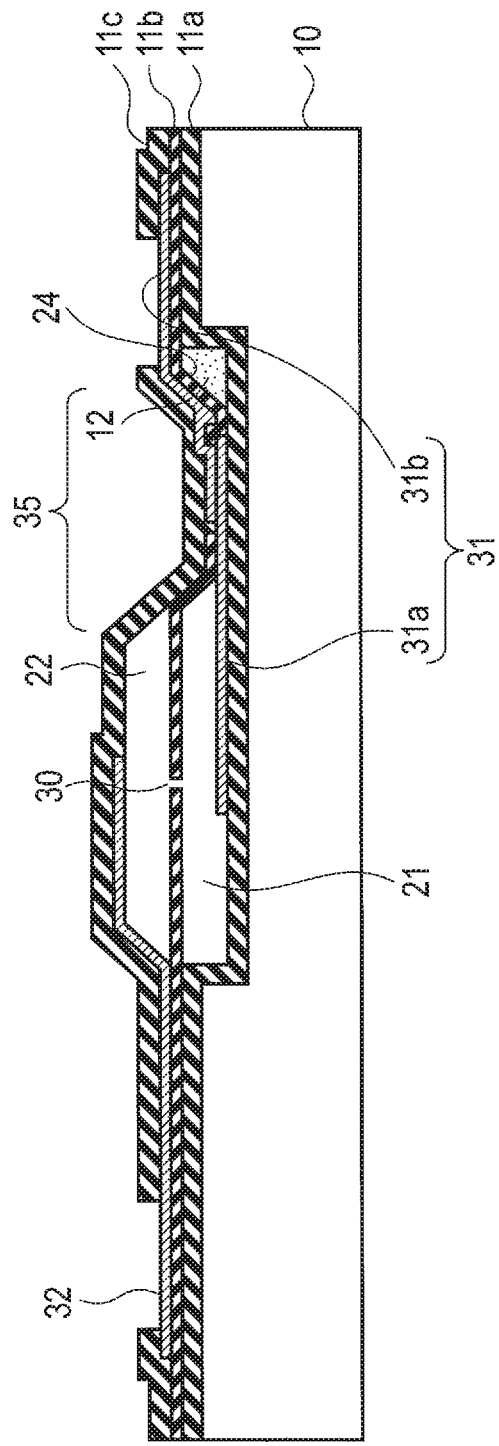
F I G. 10

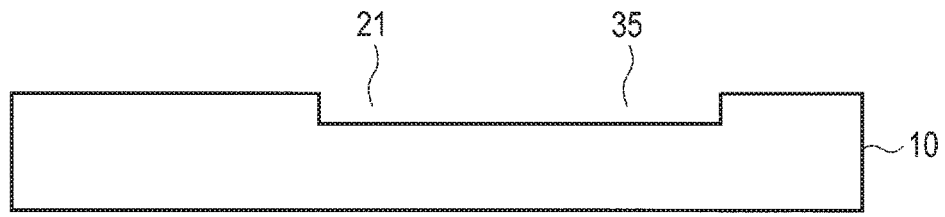
F I G. 11A
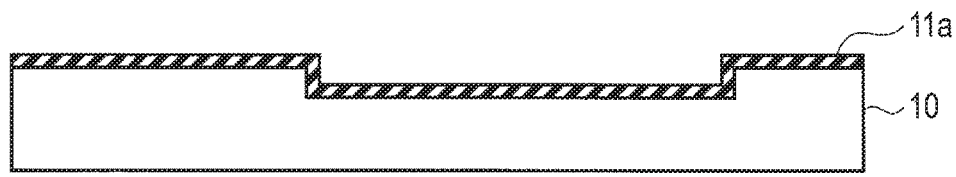
F I G. 11B
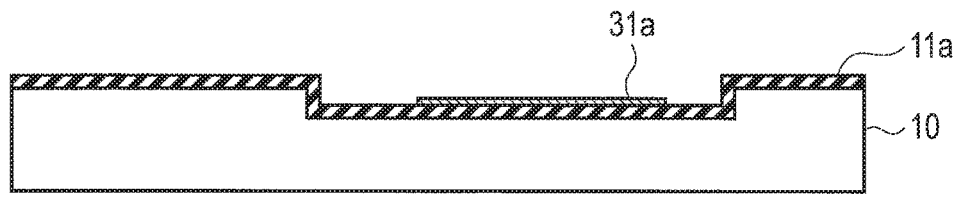
F I G. 11C
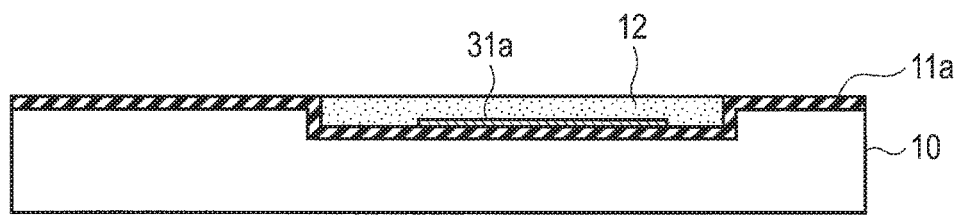
F I G. 11D
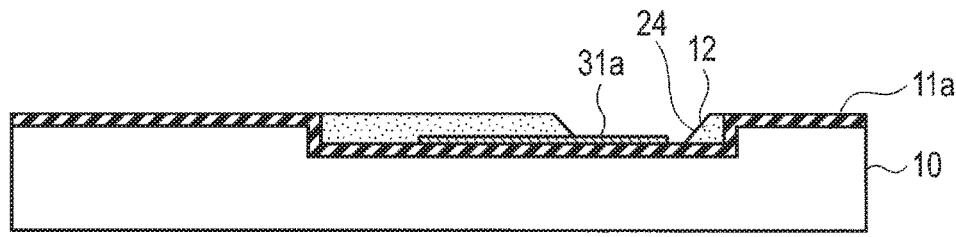
F I G. 11E

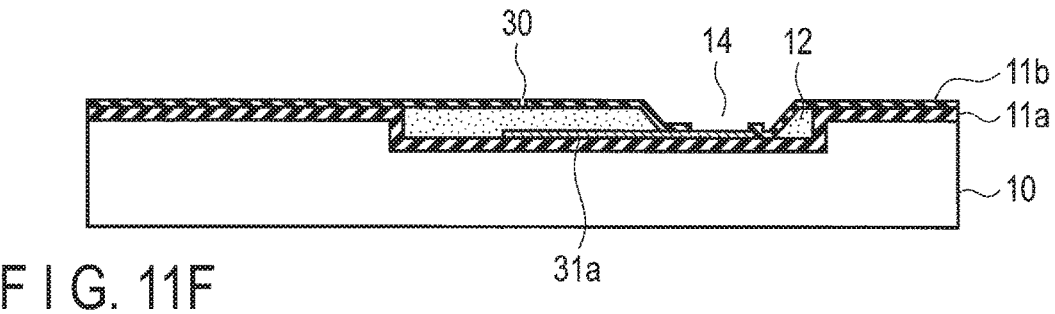
F I G. 11F
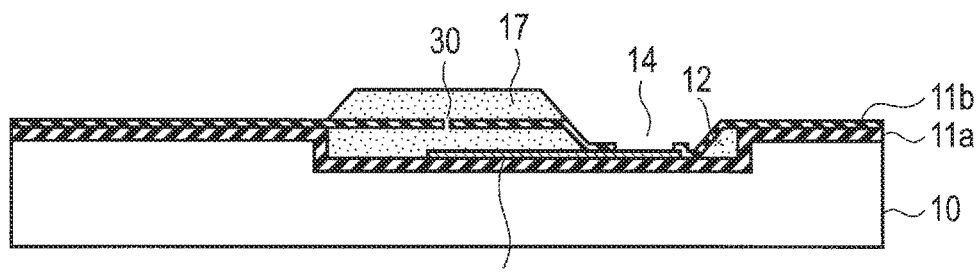
F I G. 11G
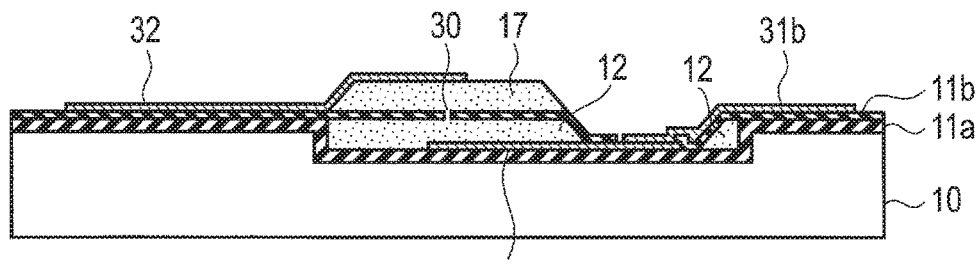
F I G. 11H
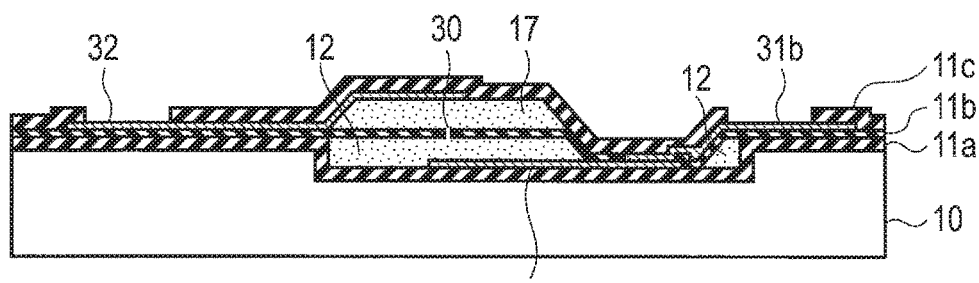
F I G. 11I

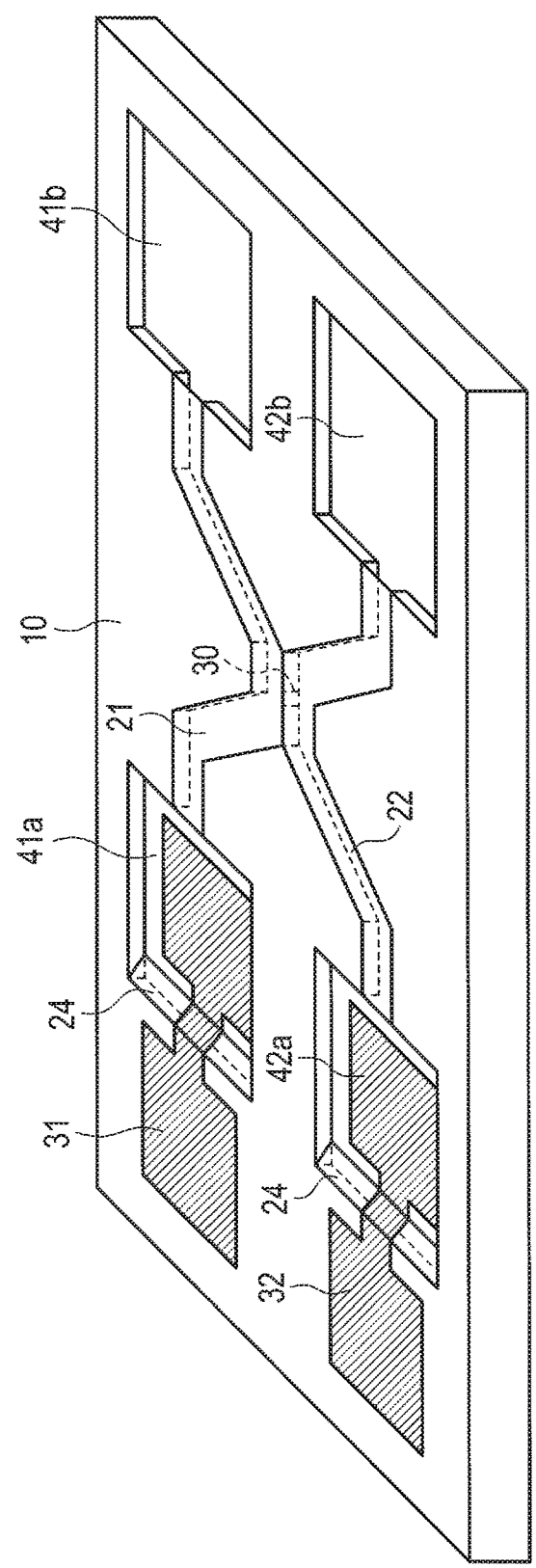
F I G. 12

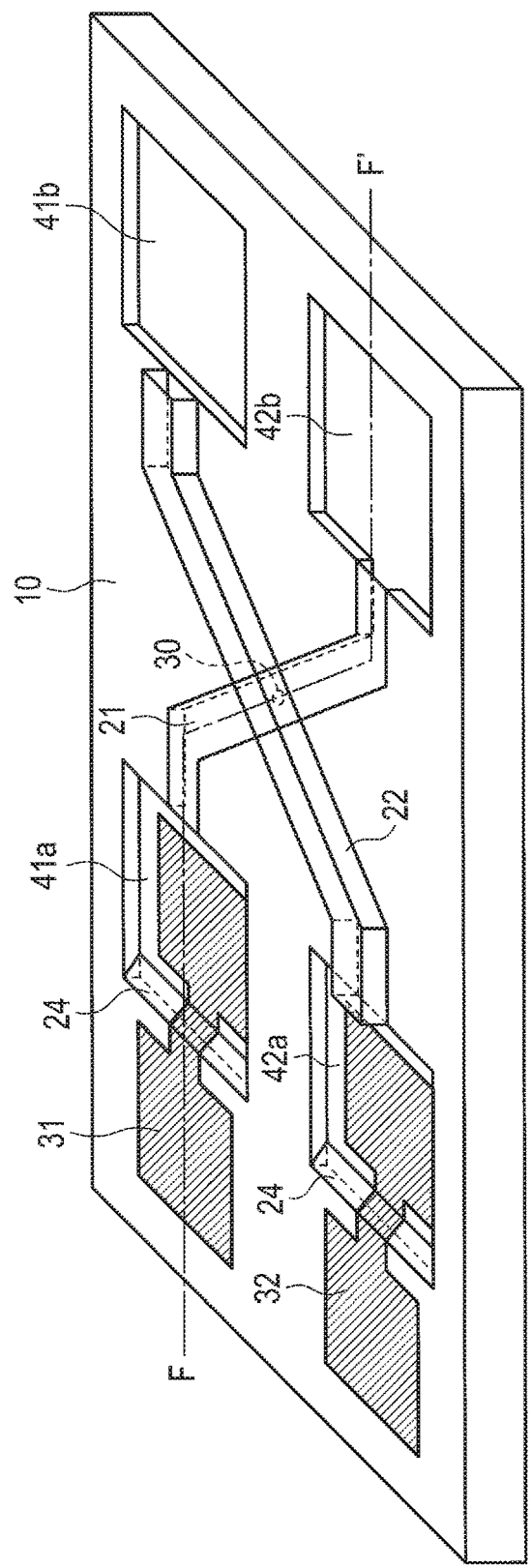
F I G. 13

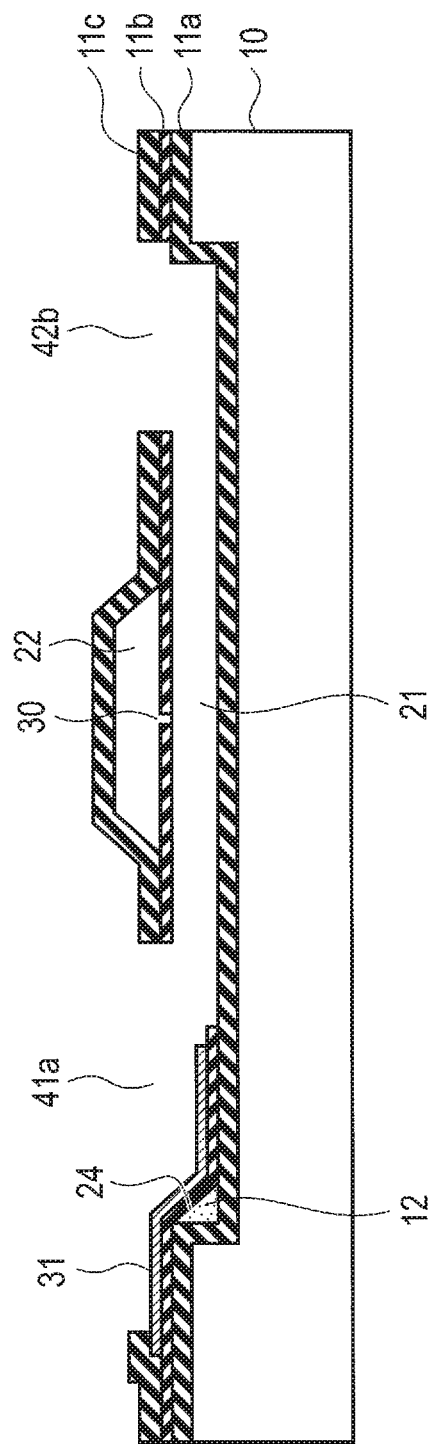
F I G. 14

F I G. 15A
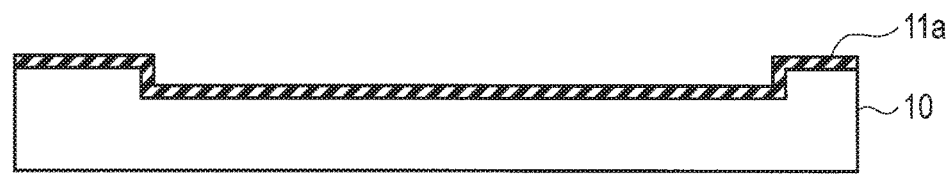
F I G. 15B
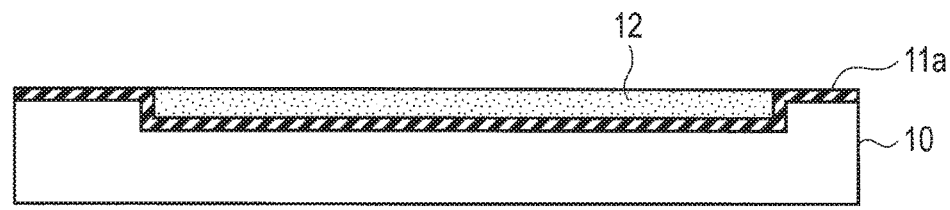
F I G. 15C
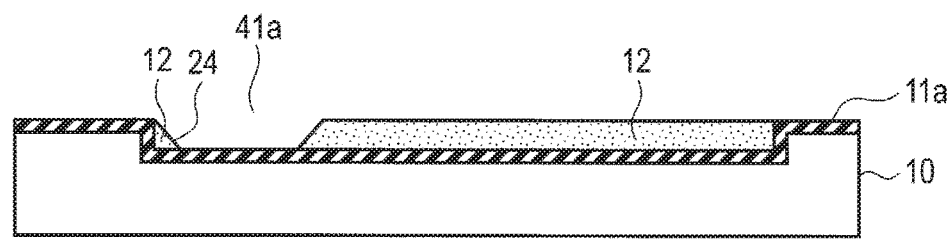
F I G. 15D
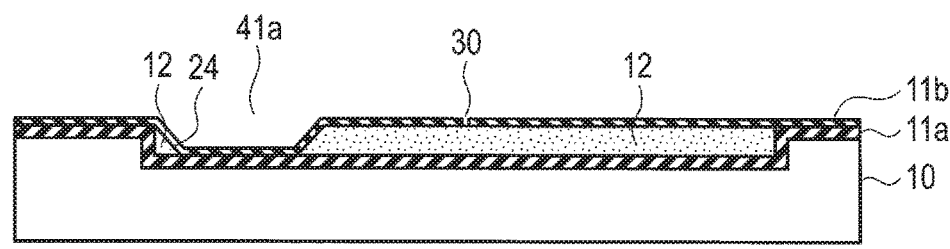
F I G. 15E

SEMICONDUCTOR MICRO-ANALYSIS CHIP AND METHOD OF MANUFACTURING THE SAME

CROSS REFERENCE TO RELATED APPLICATIONS

This application is a Continuation Application of PCT Application No. PCT/JP2015/057607, filed Mar. 10, 2015 and based upon and claiming the benefit of priority from Japanese Patent Application No. 2014-147613, filed Jul. 18, 2014, the entire contents of all of which are incorporated herein by reference.

FIELD

Embodiments described herein relate generally to a semiconductor micro-analysis chip, which is used to detect microparticles in a sample liquid, and a method of manufacturing the same.

BACKGROUND

In recent years, a semiconductor micro-analysis chip with micro flow channels formed on an Si substrate is proposed to detect microparticles in a sample liquid flowing in the channels with high sensitivity. In this analysis chip, electrodes must be provided with the micro flow channels or with reservoirs for charge (discharge) of the sample liquid those are engraved on the Si substrate. The electrodes are drawn out from the bottom surface of the micro flow channels or of the reservoir to the substrate surface. In this case, a step-disconnection of the electrode when the electrode is drawn out is a problem.

BRIEF DESCRIPTION OF THE DRAWINGS

FIG. 1 is a perspective view which shows a schematic structure of semiconductor micro-analysis chip of first embodiment.

FIG. 2 is a cross-sectional view taken along line A-A' of FIG. 1.

FIG. 4 is a perspective view which shows a schematic structure of semiconductor micro-analysis chip of second embodiment.

FIGS. 5A and 5B are cross-sectional views taken along lines B-B' and C-C' of FIG. 4, respectively.

FIGS. 6A to 6G are cross-sectional views which show a manufacturing process of the semiconductor micro-analysis chip of the second embodiment.

FIG. 7 is a perspective view which shows a schematic structure of semiconductor micro-analysis chip of third embodiment.

FIG. 9 is a perspective view which shows a schematic structure of semiconductor micro-analysis chip of fourth embodiment.

FIG. 10 is a cross-sectional view taken along line E-E' of FIG. 9.

FIGS. 11A to 11I are cross-sectional views which show a manufacturing process of the semiconductor micro-analysis chip of the fourth embodiment.

FIG. 12 is a perspective view which shows a schematic structure of semiconductor micro-analysis chip of fifth embodiment.

FIG. 13 is a perspective view which shows a schematic structure of semiconductor micro-analysis chip of sixth embodiment.

FIG. 14 is a cross-sectional view taken along line F-F' of FIG. 13.

FIGS. 15A to 15I are cross-sectional views which show a manufacturing process of the semiconductor micro-analysis chip of the sixth embodiment.

DETAILED DESCRIPTION

Figure 3A:
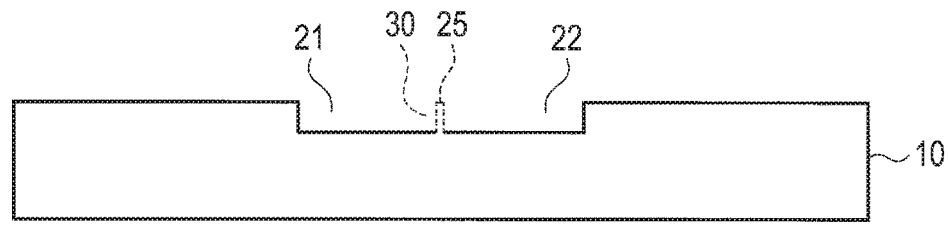
FIGS. 3A to 3F are cross-sectional views which show a manufacturing process of the semiconductor micro-analysis chip of the first embodiment.

In general, according to one embodiment, a semiconductor micro-analysis chip includes: a first flow channel provided with a substrate surface, the first flow channel engraved on the substrate into which a sample liquid can flow; micropore provided with a part of the first flow channel, the micropore through which microparticles in the sample liquid pass; a reservoir provided with at least one end of the first flow channel, the reservoir engraved on the substrate for inlet and outlet of the sample liquid; and a first electrode provided with a part of the first flow channel or of the reservoir. The first electrode is disposed from the bottom surface of the first flow channel or of the reservoir to the substrate surface, and a side surface which connects the bottom surface and the substrate surface is tapered for reducing a bend in a height direction of the first electrode.

Hereinafter, a semiconductor micro-analysis chip of each embodiment is described with reference to the accompanying drawings.

First Embodiment

FIGS. 1 and 2 show schematic structures of the semiconductor micro-analysis chip of first embodiment, and FIG. 1 is a perspective view of the chip and FIG. 2 is a cross-sectional view taken along line A-A' in FIG. 1.

In the Figure, reference number 10 denotes a semiconductor substrate, and the semiconductor substrate 10 is formed of various materials such as Si, Ge, SiC, GaAs, InP, and GaN. In the description presented below, an Si semiconductor substrate 10 is given for the sake of exemplification.

Reference numbers 41 (41a, 41b) and 42 (42a, 42b) denote reservoirs used for inlet/outlet of a sample liquid. A first reservoir 41 includes a sample liquid inlet 41a and a sample liquid outlet 41b. A second reservoir 42 includes an electrolyte solution inlet 42a and an electrolyte solution outlet 42b. The reservoirs 41 and 42 are formed as, for example, a pattern of 1 mm square engraved by 2 μm on the surface of the Si substrate 10 by performing a selective etching process or the like.

Reference number 21 denotes a first flow channel through which the sample liquid flows and reference number 22 denotes a second flow channel through which an electrolyte solution flows. The flow channels 21 and 22 are engraved in 50 μm in width and by 2 μm in depth on the Si substrate 10 in such a layout that they partly come close to each other. Furthermore, the upper part of the flow channels 21 and 22 are covered with an insulating thin film (having a thickness of 200 nm, for example) such as silicon oxide film ($SiO_2$), silicon nitride film ($SiNx$), or alumina film ($Al_2O_3$). That is, as shown in FIG. 2, a flow channel cap layer 11b (a lid to seal the flow channels) is formed on the flow channels 21 and 22. Thus, the first and second flow channels 21 and 22 are formed as tunnels engraved in the substrate.

At that time, the cap layer lib is formed within a range contacting the reservoirs 41a, 41b, 42a, and 42b. A joint part between the upper part of the reservoir and the flow channel is formed partly uncovered with the cap layer 11b to pass the sample liquid and electrolyte solution therethrough. Consequently, the flow channels 21 and 22 are shaped in tunnels which open to the corresponding reservoirs.

Reference number 30 denotes a micropore provided with a contacting part of the first flow channel 21 and the second flow channel 22. A micropore 30 is formed as a slit on a partition 25 (such as $SiO_2$ having a thickness of 0.2 μm) between the flow channels 21 and 22 by etching. The size (width) of the micropore 30 will be set slightly larger than the size of particles to be detected. If the size of microparticles to be detected is 1 μmφ, the width of the micropore 30 in FIG. 1 is set to, for example, 1.5 μm.

Reference numbers 31 and 32 denote electrodes used to detect microparticles. A first electrode 31 is formed to be partly exposed inside the first flow channel 21. A second electrode 32 is formed to be partly exposed inside the second flow channel 22. The electrodes may be structured to have a sample liquid contacting surface formed of AgCl, Pt, Au, or the like.

The electrodes 31 and 32 are, as shown in FIG. 2, provided with the bottom part of the first flow channel 21 and the second flow channel 22, respectively, interposing the micropore 30 therebetween. Each of the electrodes 31 and 32 is drawn to the surface of the substrate through the side wall of the flow channel. In the flow channels 21 and 22, each side wall used to draw out the electrode is formed as a taper 24 which forms an obtuse angle with the bottom surface of the flow channel. The taper 24 prevents step-disconnection which may occur in drawing out of each of the electrodes 31 and 32.

Note that reference number 11a in FIG. 2 denotes an $SiO_2$ film disposed on the surface of the substrate. Furthermore, since FIG. 2 is a cross-sectional view of that part including the micropore, the slit for the micropore 30 is depicted in dotted lines.

In such a structure, ion current passing through the micropore 30 is basically determined based on the size of micropore 30. That is, when an electrolyte solution (a solution in which an electrolyte is dissolved to conduct ion current therein) is filled in both the flow channels 21 and 22 and voltage is applied to each of the electrodes 31 and 32, the current flowing therein (steady-state current at the time when microparticles are not passing through the slit) is determined by the size of micropore 30. When a microparticle to be detected passes through the micropore 30, the microparticle obstructs a part of the micropore 30, and thus the ion transfer is blocked. The current flow is thus reduced corresponding to the degree of ion transfer blockage. The change in the ion current flow is determined based on a relative relationship between the micropore 30 and the microparticle in consideration of their shape, size, length, and the like. That is, when a microparticle passes through the micropore 30, the content of the microparticle can be calculated by observing a change in amount (reduction amount) of the ion current and chronological changes of the ion current.

Note that, if microparticles are conductive or surface state conductive, such microparticles transfer ion charges therebetween and current may be increased by the electrical conduction of the microparticles themselves. In that case, too, the content of the microparticle passing through the micropore 30 can be calculated by observing a change in amount (increase amount) of ion current and chronological changes of ion current.

The size of micropore 30 may be determined in consideration of the passability of microparticles to be detected and the degree of change in the ion current (sensitivity). For example, the size may be set to be 1.5 to 5 times as large as the external diameter of target particle. Furthermore, the electrolyte solution in which target particles are dissolved may be various electrolyte solutions such as KCl solution or various buffer solutions such as tris ethylene diamine tetra acetic acid (Tb) buffer solution, and phosphate buffered saline (PBS) buffer solution.

In the semiconductor micro-analysis chip of the present embodiment shown in FIGS. 1 and 2, for example, the first flow channel 21 will be used as a sample liquid inlet flow channel through which the sample liquid (a suspension in which microparticles to be detected are dispersed in the electrolyte solution) flows and drops into the reservoir 41a or 41b. Here, as described above, the flow channel 21 is formed in the tunnel shape. Thus, at the instant when the sample liquid reaches the entrance of the flow channel 21, it is sucked into the flow channel 21 by capillarity and fills the inside of the flow channel 21. The flow channel 22 is used as a receptor flow channel for the microparticles to be detected. The electrolyte solution which does not contain microparticles is dropped into the reservoir 42a or 42b and the inside of the flow channel 22 is filled with the electrolyte in the same manner. In this state, if voltage is applied to the electrodes 31 and 32, the microparticles which pass through the micropore 30 can be detected.

The polarity of the voltage applied between the electrodes 31 and 32 differs depending on charge condition of the target particle (such as bacterium, virus, and marker particle). Specifically, if the target is a negatively charged microparticle, the voltage may be applied between the first electrode 31 as a negative electrode and the second electrode 32 as a positive electrode for creating the movement of the microparticles by in-liquid electric field to pass the microparticles through the micropore. Then, in this state, the ion current observation may be performed to detect the target microparticles.

Note that the detection may be performed by filling the sample liquid in both the first flow channel 21 and the second flow channel 22. This will be effective for, particularly, a case where charge conditions of target particles are unknown or a case where positively charged particles and negatively charged particles are mixed. Note that, the detection performed by filling the sample liquid in both the first flow channel 21 and the second flow channel 22 can be adopted even if the charge condition of target particles is clear. In that case, the sample liquid and the electrolyte solution are not prepared individually and the procedure for the microparticle detection can be simplified. However, the reservoirs of the flow channels 21 and 22 (that is, the reservoirs 41a and 42a, and the reservoirs 41b and 42b) must be electrically separated, that is, the sample liquid must be independent in each reservoir.

As can be understood from the above, in the semiconductor micro-analysis chip of the present embodiment, microparticles can be detected by simply introduce the sample liquid into the chip and performing electrical observation of the sample liquid. Furthermore, the chip can be microminiaturized and mass-produced by a semiconductor processing technique, and a microparticle detection circuit and an identification determination circuit can be integrated therein. Therefore, a microminiaturized and highly-sensitive analysis chip can be mass-produced with lower costs. This leads to a highly sensitive detection process of bacteria and virus performable with facility if the chip is applied to a fast check technology for infectious pathogen and food poisoning bacteria, it can be used in such purposes as preventing an outbreak of pandemic diseases and ensuring food safety. For example, the chip is suitable for cases where bulk amount of the chips must be provided at very low costs, specifically, a case where primary fast check kits are required for diseases requiring emergency quarantine such as new influenza or the like and a case where facile food poisoning check kits are required for possible food poisoning in domestic scenes.

Furthermore, an additional substrate and a cover glass are unnecessary in forming a seal structure (lid) of the flow channels, costs for a bonding process can be reduced. Moreover, since the microparticles can be detected electrically, a noise elimination by an electronic circuit technique and high sensitization by a real-time digitization process (statistical process or the like) can be performed. In addition, since the chip does not require an element which occupies a relatively large space such as an optical system, the detection device can be drastically miniaturized as compared to a device with an optical detection scheme.

Now, with reference to FIGS. 3A to 3F, a manufacturing method of the semiconductor micro-analysis chip shown in FIGS. 1 and 2 is explained. In this section, the flow channel contacting part at which electrodes are disposed is explained in particular. FIGS. 3A to 3F are, as in the case of FIG. 2, cross-sectional views taken along line A-A' of FIG. 1.

First, the surface of Si substrate 10 is etched by, for example, 2 μm using a resist mask or an $SiO_2$ hard mask to form first and second flow channels 21 and 22 and reservoirs 41a, 41b, 42a, and 42b. Furthermore, a slit used as micropore 30 is formed in a partition 25 (having a width of 100 nm, for example) dividing the flow channels 21 and 22 at their contacting part. This is shown in FIG. 3A. The substrate 10 is etched by a depth reactive ion etching (RIE) technique such as a Bosch process for etching the side surfaces as vertical as possible.

Figure 3B:
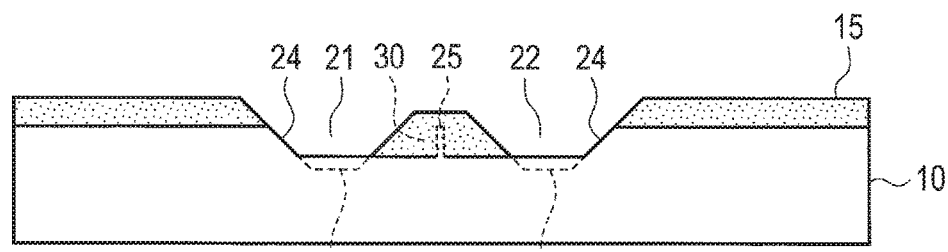

Then, as shown in FIG. 3B, the side walls of the flow channels 21 and 22 are partly etched using resist 15 as a mask to make the side walls tapered. The tapered side walls may be formed by, for example, adjusting lithography conditions to form the resist in a tapered shape, or adjusting later-performed etching conditions to perform etching pushing back the resist. At that time, the side walls are provided with taper 24 and the bottom part is over-etched. Reference number 23 in the Figure denotes the over-etched area; however, the over-etched area 23 does not have an effect on succeeding process or the structure of chip itself, and thus, it is not depicted in the following Figures.

Figure 3C:
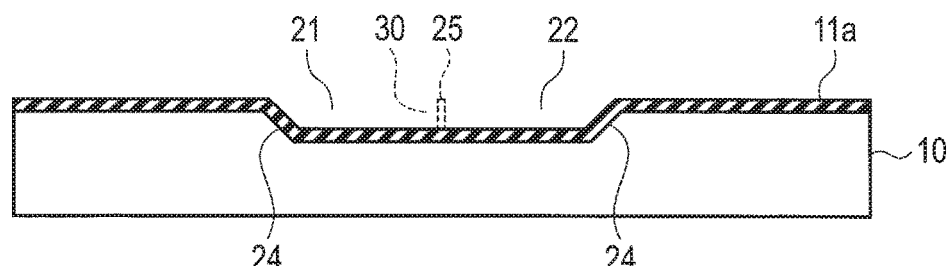

Then, as shown in FIG. 3C, an $SiO_2$ film 11a is formed on Si substrate 10 by thermal oxidation. The thermal oxidation is performed to form the $SiO_2$ film having a thickness of 200 nm using, for example, a wet oxidization technique. At that time, the partition 25 as a 100 nm width silicon between the flow channels 21 and 22 is oxidized entirely from their both sides to be an $SiO_2$ fence having a width of approximately 230 nm.

Figure 3D:
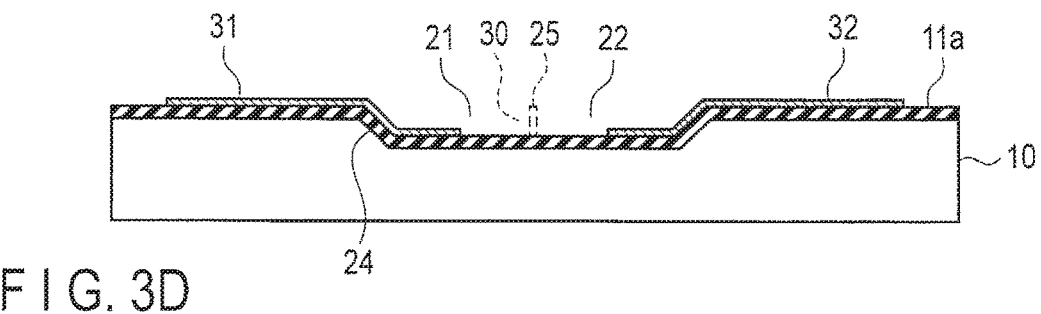

Then, as shown in FIG. 3D, first and second electrodes 31 and 32 to be drawn from the bottom part of the flow channels 21 and 22 to the substrate surface are formed. At that time, the taper 24 formed on the side walls allows the electrodes 31 and 32 to form favorably without causing step-disconnection therein. The electrodes 31 and 32 are formed by performing metal evaporation (resist heating evaporation, electron beam heating evaporation, and sputtering) to a reverse resist pattern or double-layered resist pattern (not shown) and performing lift off of the pattern, or formed by forming a resist pattern after the entire metal evaporation and etching the formed pattern. Materials for the electrodes may be Ti/Pt, Ti/Pt/Au, Ti/Pt/AgCl, and Ti/Ag/AgCl to make the liquid contacting surface AgCl, Pt, and Au.

Figure 3E:
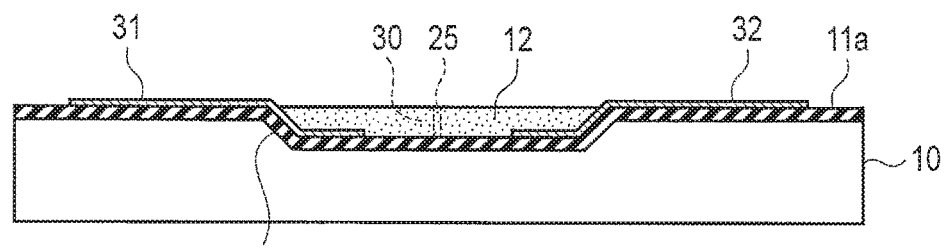

Then, as shown in FIG. 3E, sacrificial layer 12 to form a flow channel cap is embedded in the flow channels. The sacrificial layer 12 is formed of an organic material such as polyimide resin. For example, the precursor of polyimide resin is spin-coated and thermal-cured, and the surface of the $SiO_2$ film 11a and the electrodes 31 and 32 is exposed by performing chemical mechanical polishing or entire surface etching of polyimide resin. Sacrificial layer 12 may be formed of any material as long as it is selectively removable and on which an insulating film such as $SiO_2$, $SiNx$, and $Al_2O_3$ can be formed. Furthermore, the material is not limited to an organic material.

Figure 3F:
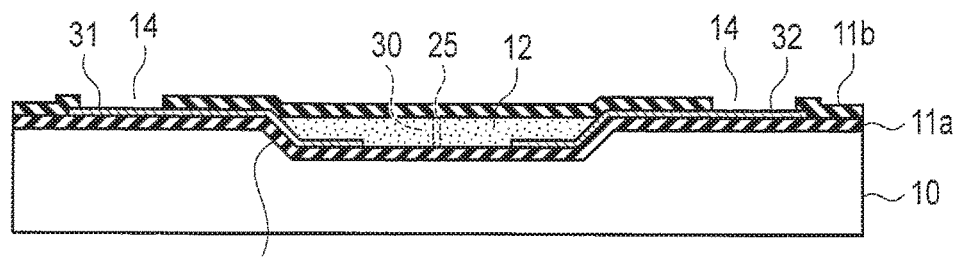

Then, as shown in FIG. 3F, an insulating film (such as $SiO_2$, $SiNx$, and $Al_2O_3$) to be a cap layer 11b is formed by CVD, sputtering, or the like. Then, a resist pattern (not shown) having an opening in a part corresponding to the reservoir and electrode pad (external connection terminal) is formed. Then, the cap layer 11b is selectively etched using the resist pattern as a mask. Through these steps, the reservoirs 41a, 41b, 42a, and 42b are partly opened and an opening 14 is formed in the cap layer 11b.

Then, the structure shown in FIG. 2 can be obtained by performing selective removal of the sacrificial layer 12 by, for example, an oxygen plasma ashing. The sacrificial layer 12 in the flow channels 21 and 22 is removed by ashing from the opening ends of the flow channels 21 and 22 by oxygen plasma. After the sacrificial layer has been removed, the flow channels 21 and 22 are surrounded by the insulating layer up and down and from right to left.

As above, the semiconductor micro-analysis chip of the present embodiment can be produced through a general semiconductor device manufacturing process using an Si substrate 10. Thus, the chip is not only utilizable for microparticle detection with high sensitivity but also applicable to microminiaturization and mass-production techniques in the semiconductor field. Therefore, the chip can be manufactured minutely at low cost. In addition, the side walls of the present embodiment used to draw out the first and second electrodes 31 and 32 have the taper 24 for preventing step-disconnections in the drawn-out portions of the electrodes 31 and 32. That is, the reliability as a detection device can be improved.

Second Embodiment

FIGS. 4, 5A and 5B show schematic structures of semiconductor micro-analysis chip of second embodiment. FIG. 4 is a perspective view of the chip, FIG. 5A is a cross-sectional view taken along line B-B' in FIG. 4, and FIG. 5B is a cross-sectional view taken along line C-C' in FIG. 4. Note that the structural elements already shown in FIGS. 1 and 2 are referred to by the same reference numbers and their detailed descriptions are omitted.

The present embodiment differs from the first embodiment in respect of a groove connecting flow channels 21 and 22, the groove disposed in the proximity of micropore 30 for drawing out electrodes.

As shown in FIG. 5B, first electrode 31 (31a, 31b) and second electrode 32 (32a, 32b) are formed from the bottom part of the flow channels 21 and 22 and from the bottom part of the groove 35 connecting the flow channels 21 and 22 to the substrate surface. That is, at the bottom of the groove 35 connecting the flow channels 21 and 22, the electrode portions 31a and 32a are formed individually. The flow channels 21 and 22 are separated from the groove 35 by the cap layer 11b. The sacrificial layer 12 resides at side surfaces of the groove 35 opposite to the flow channels 21 and 22 to be a taper 24 on the side walls of the groove 35. Drawn-out portions 31b and 32b are formed on the cap layer 11b connected to the electrode portions 31a and 32a.

Now, with reference to FIGS. 6A to 6G, a manufacturing method of the semiconductor micro-analysis chip shown in FIGS. 4, 5A, and 5B is explained. In this section, the flow channel contacting part at which electrodes are disposed is explained in particular. FIGS. 6A to 6G are, as in the case of FIG. 5B, cross-sectional views taken along line C-C' of FIG. 4.

First, as in the first embodiment, the surface of Si substrate 10 is etched to form first and second flow channels 21 and 22 and reservoirs 41a, 41b, 42a, and 42b. Furthermore, a slit used as micropore 30 is formed in a partition 25 (having a width of 100 nm, for example) dividing the flow channels 21 and 22 at their contacting part. Furthermore, a groove 35 (35a, 35b) is formed at the part where the electrodes 31 and 32 are formed. The groove 35 is connected to the flow channels 21 and 22 while extending in a direction crossing the flow channels 21 and 22.

Next, as shown in FIG. 6B, an $SiO_2$ film 11a is formed on the surface of Si substrate 10 by thermal oxidation. Thus, the partition 25 between the flow channels becomes an $SiO_2$ fence as in the first embodiment.

Then, as shown in FIG. 6C, electrode portions 31a and 32a are formed, respectively, from the bottom of the flow channels 21 and 22 to the bottom of the grooves 35a and 35b. That is, the electrode portion 31a is formed at the first flow channel 21 side while the electrode portion 32a is formed at the second flow channel 22 side. The method and materials for forming the electrode portions 31a and 32a are the same as the electrode formation in the first embodiment.

Then, as shown in 6D, a sacrificial layer 12 used to form a flow channel cap is embedded in the flow channel part. The method and materials for forming the sacrificial layer 12 are the same as in the first embodiment.

Then, as shown in 6E, the sacrificial layer 12 within the grooves 35a and 35b is patterned. That is, the sacrificial layer 12 is patterned to reside in the flow channels 21 and 22 and at the outer side walls of the grooves 35a and 35b. At that time, a taper 24 is formed in the sacrificial layer 12 at the outer side wall of each of the grooves 35a and 35b.

Then, as shown in FIG. 6F, an insulating film used as a flow channel cap layer 11b is formed as in the first embodiment. Then, the cap layer 11b is selectively etched to provide openings with the reservoirs and electrode pad (external connection terminal) parts.

Then, as shown in FIG. 6G, drawn-out portions 31b and 32b are formed. That is, a drawn-out portion 31b is formed at the first flow channel 21 side to be connected to the upper surface of the electrode portion 31a and drawn out on the cap layer 11b. Furthermore, a drawn-out portion 32b is formed at the second flow channel 22 side to be connected to the upper surface of the electrode portion 32a and drawn out on the cap layer 11b. The method and materials for forming the drawn-out portions 31b and 32b are the same as those for the electrode portions 31a and 32a.

Then, the structure shown in FIG. 5B can be obtained by performing selective removal of the sacrificial layer 12 by, for example, oxygen plasma ashing.

As can be understood from the above, the side walls of the present embodiment used to draw out the first and second electrodes 31 and 32 have the taper 24 for preventing step-disconnections in the drawn-out portions of the electrodes 31 and 32. Therefore, the same advantage as in the first embodiment can be achieved.

Third Embodiment

Figure 8:
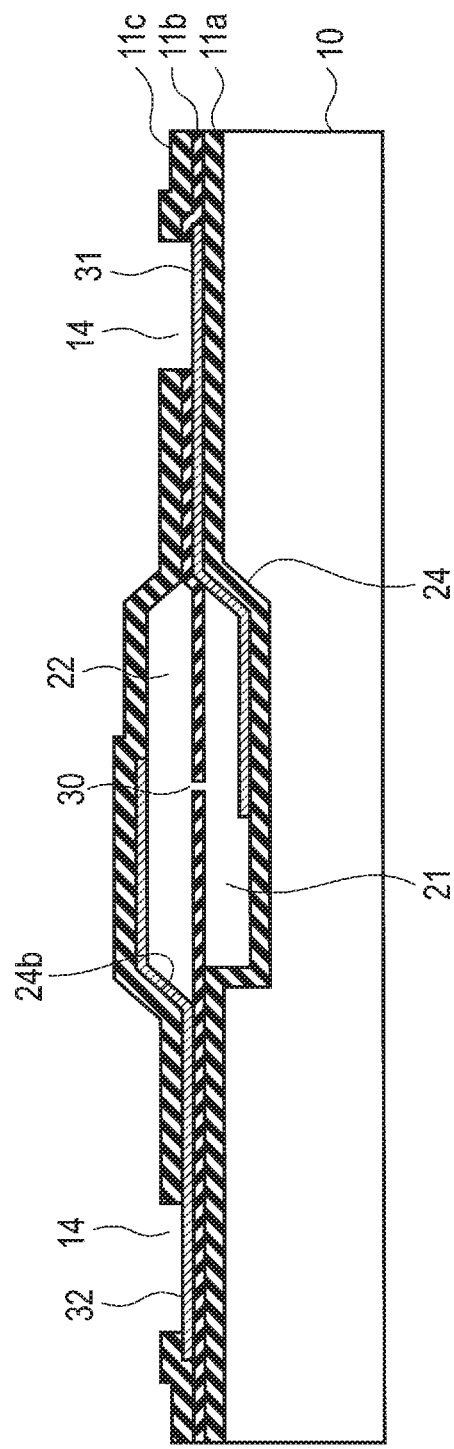
FIG. 8 is a cross-sectional view taken along line D-D' of FIG. 7.

FIGS. 7 and 8 show schematic structures of semiconductor micro-analysis chip of third embodiment. FIG. 7 is a perspective view of the chip, FIG. 8 is a cross-sectional view taken along line D-D' in FIG. 7. Note that the structural elements already shown in FIGS. 1 and 2 are referred to by the same reference numbers and their detailed descriptions are omitted.

In this embodiment, first flow channel 21 and second flow channel 22 are in a crossing arrangement. The first flow channel 21 is formed by engraving an Si substrate as an engraved type tunnel flow channel. The second flow channel 22 is formed of an insulating film (cap layer) 11c as a convex insulating film tunnel on the substrate surface. Furthermore, a micropore 30 is formed at the crossing point of two flow channels 21 and 22. The micropore 30 can be shaped optionally.

Note that, although two flow channels 21 and 22 are arranged to cross each other in the above description, they may be arranged to return to their respective flow channel side at the part where they are layered to contact each other. Or, two flow channels 21 and 22 may be formed as tunnel flow channels which are partly close to each other, not crossing each other.

First and second electrodes 31 and 32 are formed in the proximity of the micropore 30 between the flow channels 21 and 22. The first electrode 31 is formed to be partly exposed at the bottom of the first flow channel 21 and is drawn out to the substrate surface through the flow channel side wall. In the first flow channel 21, the side wall used to draw out the electrode 31 is formed as a taper 24 which forms an obtuse angle with the bottom surface of the flow channel. Furthermore, the second electrode 32 is formed to be partly exposed at the upper surface of the inside wall of the second flow channel 22 and is drawn out to the substrate surface through the flow channel side wall. In the second flow channel 22, the side wall used to draw out the electrode 32 is formed as a taper 24b which forms an obtuse angle with the upper surface of the flow channel. That is, the tapers 24 and 24b are formed at the side walls used to draw out the electrodes 31 and 32 to form an obtuse angle with the bottom surface and the upper surface of the flow channel. Thus, step-disconnections during drawing out of the electrodes 31 and 32 can be prevented.

Therefore, the same advantage obtained in the first embodiment can be achieved in this structure.

Fourth Embodiment

FIGS. 9 and 10 show schematic structures of semiconductor micro-analysis chip of fourth embodiment. FIG. 9 is a perspective view of the chip, FIG. 10 is a cross-sectional view taken along line E-E' in FIG. 9. Note that the structural elements already shown in FIGS. 1 and 2 are referred to by the same reference numbers and their detailed descriptions are omitted.

The present embodiment differs from the third embodiment in respect of a groove 35 connected to a flow channel 21, the groove 35 disposed in the proximity of micropore 30 for drawing out a first electrode 31 therethrough. A second electrode 32 at a second flow channel 22 side is drawn out as described in the third embodiment.

As shown in FIG. 10, a first electrode 31 (31a, 31b) is formed from the bottom of the first flow channel 21 and from the bottom of the groove 35 which connects to the flow channel 21 to the substrate surface. That is, the electrode portion 31a is formed at the bottom of the groove 35 which connects to the flow channel 21. A drawn-out portion 31b connected to the upper surface of the electrode portion 31a is drawn out on the upper surface of the cap layer 11b. Here, a sacrificial layer 12 resides on a side surface opposite to the flow channel 21 of the groove 35 as a taper 24 on the side wall of the groove 35.

Now, with reference to FIGS. 11A to 11I, a manufacturing method of the semiconductor micro-analysis chip shown in FIGS. 9 and 10 is explained. In this section, the flow channel contacting part at which electrodes are disposed is explained in particular. FIGS. 11A to 11I are, as in the case of FIG. 10, cross-sectional views taken along line E-E" of FIG. 9.

First, the surface of Si substrate 10 is etched to form first flow channel 21 and reservoirs 41a, 41b, 42a, and 42b. Furthermore, a groove 35 is formed to be connected to the flow channel 21 at the part where the first electrode 31 is formed and to extend in a direction perpendicular to the flow channel 21. This is FIG. 11A.

Next, as shown in FIG. 11B, an $SiO_2$ film 11a is formed on the surface of Si substrate 10 by thermal oxidation.

Then, as shown in FIG. 11D, the electrode portion 31a of the first electrode 31 is formed at the bottom of the first flow channel 21.

Then, as shown in FIG. 11D, the sacrificial layer 12 used to form a flow channel cap is embedded in the flow channel part.

Then, as shown in FIG. 11E, the sacrificial layer 12 within the groove 35 is patterned. That is, the sacrificial layer 12 is patterned to reside in the flow channel 21 and at the outer side wall of the groove 35. At that time, a taper 24 is formed in the sacrificial layer 12 at the outer side wall of the groove 35.

Then, as shown in FIG. 11F, an insulating film used as a flow channel cap layer 11b is formed by a method such as CVD and sputtering. Then, the cap layer 11b is selectively etched to provide an opening 14 on the reservoir and electrode pad (external connection terminal) part. Furthermore, a micropore 30 is formed at the part crossing the second flow channel 22 by a method such as RIE.

Then, as shown in FIG. 11G, a sacrificial layer 17 formed of polyimide resin is formed on the cap layer 11b to cross the pattern for the first flow channel. At that time, the sacrificial layer 17 patterned for the second flow channel is formed in a trapezoidal shape whose upper side is shorter than its lower side.

Then, as shown in FIG. 11H, a drawn-out portion 31b of the first electrode 31 and the second electrode 32 are formed. At that time, the drawn-out portion 31b of the first electrode 31 can be formed without step-disconnection since the side wall of the groove 35 is in a taper shape by patterning the sacrificial layer 12. Furthermore, the second electrode 32 can be formed without step-disconnection since the pattern for the second flow channel is formed in a trapezoidal shape.

Then, as shown in FIG. 11I, an $SiO_2$ cap layer 11c is formed by a method such as plasma CVD. Then, an opening is formed by removing $SiO_2$ in the sample inlet and outlet area at an end of the flow channel. Then, the sacrificial layers 12 and 17 are removed by, for example, $O_2$ ashing through the opening to form the tunnel flow channels in a crossing multilayer arrangement.

As can be understood from the above, the side walls of the present embodiment used to draw out the first and second electrodes 31 and 32 have the taper 24 for preventing step-disconnection in the drawn-out portions of the electrodes 31 and 32. Therefore, the same advantage as in the first embodiment can be achieved.

Fifth Embodiment

FIG. 12 is a perspective view which shows a schematic structure of semiconductor micro-analysis chip of fifth embodiment. Note that the structural elements already shown in FIG. 1 are referred to by the same reference numbers and their detailed descriptions are omitted.

The present embodiment differs from the first embodiment in respect of electrodes provided with reservoirs instead of the proximity to micropore 30.

That is, a first electrode 31 is formed at the bottom of inlet side reservoir 41a to the substrate surface, and a second electrode 32 is formed at the bottom of inlet side reservoir 42a to the substrate surface. Note that a taper 24 is formed in each of the inlet side reservoirs 41a and 42a at its wall surface opposite to the flow channel. That is, the taper 24 is formed at each of the side walls used to draw out the electrodes 31 and 32 forming an obtuse angle with the bottom surface of the reservoirs. Thus, step-disconnection during drawing out of the electrodes 31 and 32 can be prevented.

Therefore, the same advantage as in the first embodiment can be achieved. Furthermore, since the electrodes 31 and 32 are formed in the reservoirs 41a and 42a, the area of the electrode can be enlarged.

Sixth Embodiment

FIGS. 13 and 14 show schematic structures of semiconductor micro-analysis chip of sixth embodiment. FIG. 13 is a perspective view of the chip, FIG. 14 is a cross-sectional view taken along line F-F' in FIG. 13. Note that the structural elements already shown in FIGS. 1 and 2 are referred to by the same reference numbers and their detailed descriptions are omitted.

The present embodiment differs from the fifth embodiment in respect of a cross arrangement of the first flow channel 21 and the second flow channel 22. The first flow channel 21 is formed by engraving an Si substrate as an engraved type tunnel flow channel. The second flow channel 22 is formed of an insulating film (cap layer) 11c as a convex insulating film tunnel on the substrate surface. Furthermore, a micropore 30 is formed at the crossing point of two flow channels 21 and 22 in the cap layer 11b. The micropore 30 can be shaped optionally.

Note that, although two flow channels 21 and 22 are arranged to cross each other in the above description, they may be arranged to return to their respective flow channel side at the part where they are layered to contact with each other. Or, two flow channels 21 and 22 may be formed as tunnel flow channels which are partly close to each other, not crossing each other.

The first and second electrodes 31 and 32 are, as in the fifth embodiment, formed at the bottoms of the inlet side reservoirs 41a and 42a, respectively, to the substrate surface. A taper 24 is formed in each of the inlet side reservoirs 41a and 42a at its wall surface opposite to the flow channel. Thus, step-disconnections during drawing out of the electrodes 31 and 32 can be prevented.

Now, with reference to FIGS. 15A to 15I, a manufacturing method of the semiconductor micro-analysis chip shown in FIGS. 13 and 14 is explained. In this section, the flow channel contacting part at which, electrodes are disposed is explained in particular. FIGS. 15A to 15I are, as in the case of FIG. 14, cross-sectional views taken along line E-E' of FIG. 13.

First, the surface of Si substrate 10 is etched to form first flow channel 21 and reservoirs 41a, 41b, 42a, and 42b. This is FIG. 15A.

Next, as shown in FIG. 15B, an $SiO_2$ film 11a is formed on the surface of Si substrate 10 by thermal oxidation.

Then, as shown in FIG. 15C, a sacrificial layer 12 used to form a flow channel cap is embedded in the flow channel part and reservoirs.

Then, as shown in FIG. 15D, the sacrificial layer 12 within the reservoirs 41a and 42a is patterned. That is, the sacrificial layer 12 is patterned to reside in the flow channel 21 and at the outer side wall of the reservoirs 41a and 42a. At that time, a taper 24 is formed in the sacrificial layer 12 at the outer side wall of the reservoirs 41a and 42a.

Then, as shown in FIG. 15E, an insulating film used as a flow channel cap layer 11b is formed by a method such as CVD and sputtering. Then, a micropore 30 is formed at the part crossing the second flow channel 22 by a method such as RIE.

Figure 15F:
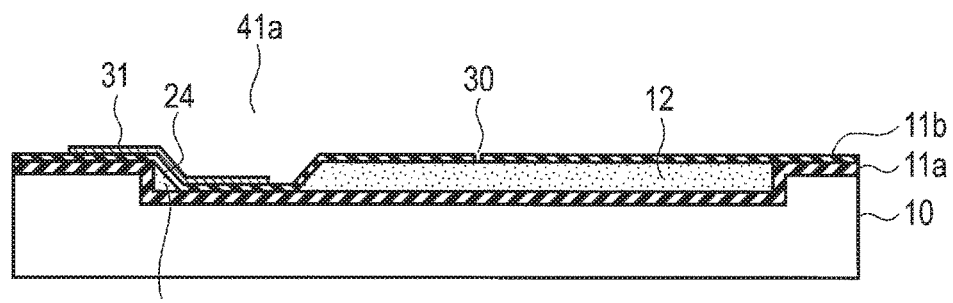

Then, as shown in FIG. 15F the electrodes 31 and 32 are formed at the bottoms of the reservoirs 41a and 42a to the substrate surface.

Figure 15G:
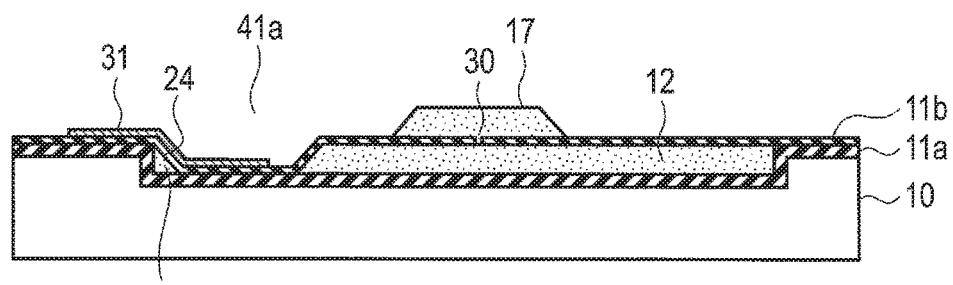

Then, as shown in FIG. 15G, a sacrificial layer 17 is formed on a first $SiO_2$ cap layer to cross the pattern for the first flow channel. At that time, the sacrificial layer 17 patterned for the second flow channel is formed in a trapezoidal shape whose upper side is shorter than its lower side.

Figure 15H:
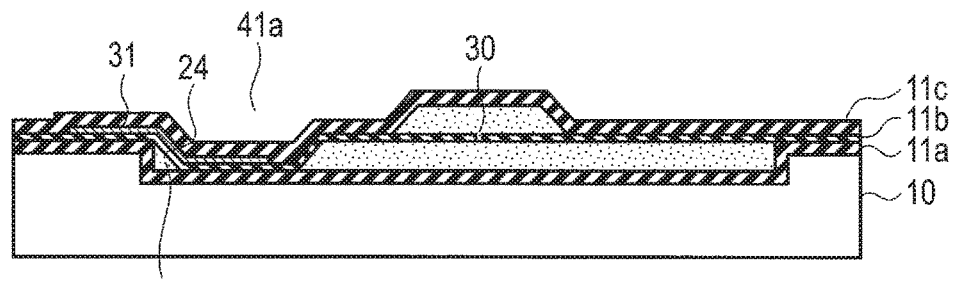

Then, as shown in FIG. 15H, an $SiO_2$ cap layer 11c is formed by a method such as plasma CVD.

Figure 15I:
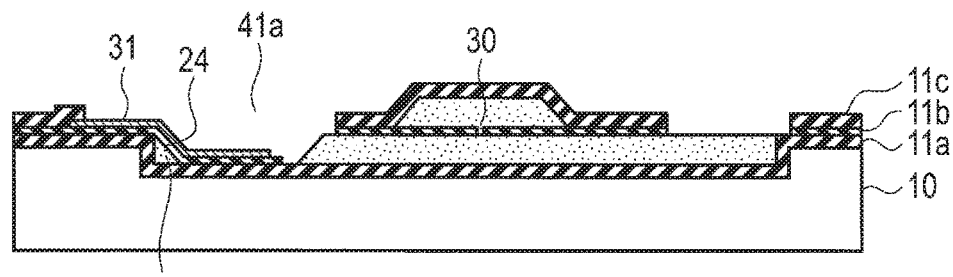

Then, as shown in FIG. 15I, an opening is formed by removing $SiO_2$ in the sample inlet and outlet area at the reservoirs. Then, the sacrificial layers 12 and 17 are removed by, for example, $O_2$ ashing through the opening to form the tunnel flow channels in a crossing multilayer arrangement.

As can be understood from the above, since the taper 24 is formed at each of the side walls used to draw out the electrodes 31 and 32, step-disconnections during drawing out of the electrodes 31 and 32 can be prevented. Therefore, the same advantage as in the first embodiment can be achieved. Furthermore, as in the fifth embodiment, the area of the electrode can be enlarged.

Seventh Embodiment

Figure 16A:
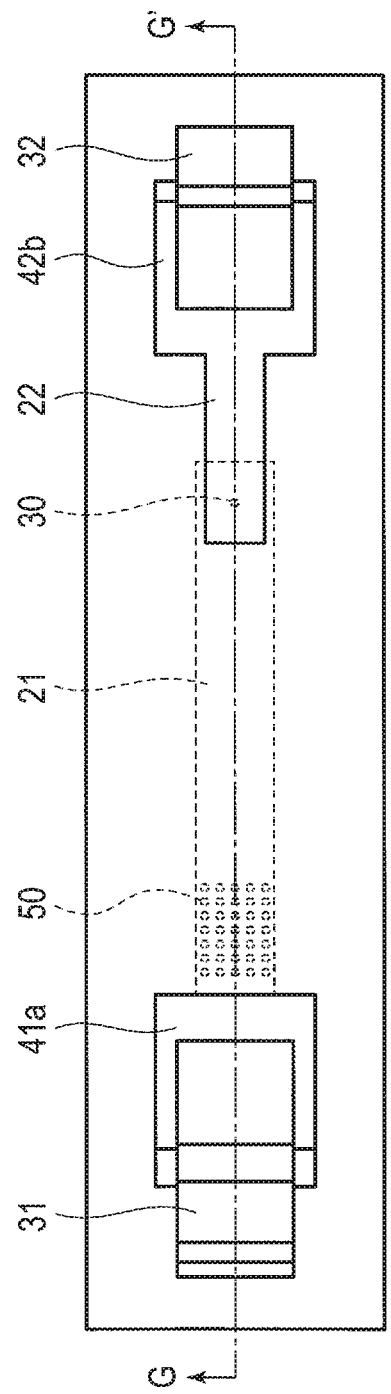
FIGS. 16A and 16B are plan views which show a schematic structure of semiconductor micro-analysis chip of the seventh embodiment.
Figure 16B:
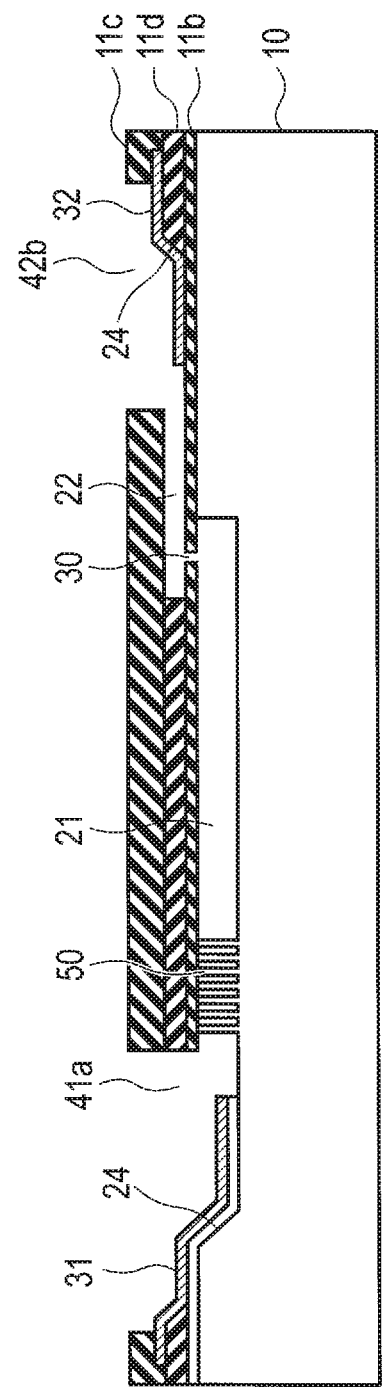

FIGS. 16A and 16B show schematic structures of semiconductor micro-analysis chip of seventh embodiment. FIG. 16A is a perspective view of the chip, FIG. 16B is a cross-sectional view taken along line G-G' in FIG. 16A.

In the present embodiment, an insulating film (cap layer) 11b, insulating film (spacer layer) 11d, and insulating film (cap layer) 11c are layered on an Si substrate 10. The insulating films 11b to 11d may be formed of a dielectric such as $SiO_2$, $Si_3N_4$, and $Al_2O_3$, or a polymeric material such as polyimide. Note that, although this is not shown in the Figure, an $SiO_2$ film 11a may be formed on the surface of the Si substrate 10 as in the above embodiments.

A first flow channel 21 is engraved on the surface of the Si substrate by, for example, 2 μm. The flow channel 21 is connected to reservoir 41a at the sample liquid inlet side. A pillar array 50 starting from the bottom surface of the flow channel toward the upper surface of the flow channel is formed at the reservoir 41a side in the first flow channel 21.

The cap layer 11b is formed as a lid over the first flow channel 21, and a micropore 30 is formed at a part thereof. The spacer layer 11d is provided for the inlet side reservoir 41a, outlet side reservoir 41b, and second flow channel 22. The cap layer 11c is formed as a lid over the second flow channel 22, and the inlet side reservoir 41a and the outlet side reservoir 42b are formed at a part thereof.

Micropore 30 is opened on the upper surface of the first flow channel 21 passing through the bottom surface of the second flow channel 22. Thus, the first flow channel 21 and the second flow channel 22 are connected spatially through micropore 30.

That is, a first electrode 31 is formed at the bottom of inlet side reservoir 41a to the substrate surface, and a second electrode 32 is formed at the bottom of inlet side reservoir 42b to the substrate surface. Note that a taper 24 is formed in each of the reservoirs 41a and 42b at its wall surface opposite to the flow channel. That is, the taper 24 is formed at each of the side walls used to draw out the electrodes 31 and 32 forming an obtuse angle with the bottom surface of the reservoirs. Thus, step-disconnections during drawing out of the electrodes 31 and 32 can be prevented.

In the semiconductor micro-analysis chip with the above-described structure, if a sample liquid (a suspension containing microparticles to be detected) is injected into the reservoir 41a, it flows into the flow channel 21 by capillarity and reaches micropore 30. Then, the second flow channel 22 is filled with a conductive electrolyte solution containing no sample microparticles. The microparticles in the sample liquid move inside the flow channel together with the sample liquid flow by capillarity in the first flow channel 21. Here, the sample microparticles may be forcedly electrophoresed on the voltage applied between the electrodes 31 and 32.

Then, voltage is applied between the electrodes 31 and 32 to observe ion current flowing therebetween. As in the first embodiment, the contents of the microparticles passing through the micropore 30 can be identified from the observed changes in ion current.

As can be understood from the above, since the taper 24 is formed at each of the side walls used to draw out the electrodes 31 and 32, step-disconnections during drawing out of the electrodes 31 and 32 can be prevented. Therefore, the same advantage as in the first embodiment can be achieved.

Furthermore, by arranging pillars starting from the bottom surface of the flow channel to the upper surface of the flow channel at suitable intervals in the flow channel 21, the pillar array 50 can be formed. The pillar array 30 can trap unnecessary particles having a relatively large size while pass through only microparticles having a small size downstream. For example, if the target is virus whose size is approximately 100 nm, the nanopillar interval will be set to 250 nm. With such a pillar array, a case where a mega particle whose size is 0.5 μm or more blocks micropore 30 can be prevented. Furthermore, if the pillar intervals and array length are adjusted suitably, the maximum size of the microparticle reaching micropore 30 can be uniformed. In this case, values above a certain point in the peak current values in ion current chances to be detected are acknowledged as a part of noise distribution, and thus, the detection can be performed with higher accuracy.

Note that the pillar array 50 may additionally be formed in the second flow channel 22 to block a backward flow of dust from the outlet opening side. Or, a slit shaped flow channel array (nanowall) or the like may be formed instead of the nanopillar 50. Furthermore, the above-mentioned pillar array can be applied to the structures of the first to sixth embodiments.

(Variations)

Note that the present invention is not limited to the above-described embodiments.

In the embodiments, Si substrate is used for exemplification; and the substrate is not necessarily limited to Si and any other semiconductor materials can be used for the substrate as long as it is treated in the ordinary semiconductor manufacturing process. Furthermore, dielectrics ($SiO_2$, SiNx, and $Al_2O_3$) are exemplified as insulating films, and their types and compositions can be chosen optionally. In addition, organic insulating films can be used. Thus, no limitation is intended by the above-described embodiments.

Furthermore, as in the third and fourth embodiments, if the flow channels are formed as a substrate engraved type at one and an insulating film tunnel type at the other, the substrate engraved type flow channel is affected largely by the step in the side wall in general. Thus, a taper may be provided with only in the substrate engraved type flow channel for preventing step-disconnections in the electrodes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A semiconductor microanalysis chip, comprising:
    a first flow channel provided at a substrate surface, the first flow channel being engraved in the substrate and being configured to have a sample liquid flow therein;
    a micropore provided at a part of the first flow channel, the micropore being configured to have microparticles in the sample liquid pass therethrough;
    a reservoir provided at at least one end of the first flow channel, the reservoir being engraved in the substrate and providing an inlet and outlet for the sample liquid;
    a first electrode provided in proximity to the micropore of the first flow channel; and
    a groove provided in an area where the first electrode is provided, the groove having a bottom surface that is engraved to a same depth as the first flow channel,
    wherein the first electrode includes (i) an electrode portion formed at a bottom surface of the first flow channel in proximity to the micropore and extending to the bottom surface of the groove, (ii) and a drawn-out portion contacting an upper surface of the electrode portion and being drawn out on the substrate surface, and
    wherein the bottom surface of the groove forms an obtuse angle with a side wall surface in the area where the first electrode is provided.

2. The chip of claim 1, further comprising a second flow channel provided at the substrate surface and having a part close to the first flow channel, the second flow channel being engraved in the substrate and being configured to have the sample liquid or an electrolyte solution flow therein,
    wherein the micropore is provided at a closest point of the first and second flow channels.

3. The chip of claim 2, further comprising a second electrode at a part of the second flow channel,
    wherein the second electrode is provided from a bottom surface of the second flow channel to the substrate surface, and
    wherein a side wall surface which connects the bottom surface of the second flow channel and the substrate surface is tapered to reduce a bend in a height direction of the second electrode.

4. The chip of claim 3, wherein the bottom surface of the second flow channel forms an obtuse angle with a side wall surface in an area where the second electrode is provided.

5. The chip of claim 1, further comprising a second flow channel provided on the substrate surface and having a part that crosses the first flow channel, the second flow channel comprising an insulating film tunnel and being configured to have the sample liquid or an electrolyte solution flow therein,
    wherein the micropore is provided at a crossing point of the first and second flow channels.

6. The chip of claim 5, further comprising a second electrode at a part of the second flow channel,
    wherein the second electrode is provided from an inner wall upper surface of the second flow channel to the substrate surface, and
    wherein the inner wall upper surface of the second flow channel forms an obtuse angle with a side wall surface in an area where the second electrode is provided.

7. The chip of claim 1, further comprising a plurality of pillars inside the first flow channel, the pillars extending from the bottom surface to an upper surface of the first flow channel.

8. A semiconductor microanalysis chip, comprising:
    a first flow channel provided at a substrate surface, the first flow channel being engraved in the substrate and being configured to have a sample liquid flow therein;
    a second flow channel provided at the substrate surface and having a part close to or crossing the first flow channel, the second flow channel being configured to have the sample liquid or an electrolyte solution flow therein;
    a micropore provided at a closest point or a crossing point of the first and second flow channels, the micropore being configured to have microparticles in the sample liquid pass therethrough;
    first reservoirs provided at both ends of the first flow channel, the first reservoirs being engraved in the substrate and providing an inlet and outlet for the sample liquid;
    second reservoirs provided at both ends of the second flow channel, the second reservoirs being engraved in the substrate and providing an inlet and outlet for the sample liquid or the electrolyte solution;
    a first electrode provided at a part of the first flow channel;
    a second electrode provided at a part of the second flow channel; and
    a groove provided in an area where the first electrode is provided, the groove having a bottom surface that is engraved to a same depth as the first flow channel,
    wherein the first electrode includes (i) an electrode portion formed at a bottom surface of the first flow channel in proximity to the micropore and extending to the bottom surface of the groove, and (ii) a drawn-out portion contacting an upper surface of the electrode portion and being drawn out on the substrate surface via the groove, and wherein the bottom surface of the groove forms an obtuse angle with a side wall surface in the area where the first electrode is provided.

9. The chip of claim 8, wherein:

the second flow channel is engraved in the substrate and has a part close to the first flow channel, the second electrode is provided from a bottom surface of the second flow channel to the substrate surface, and a side wall surface which connects the bottom surface of the second flow channel and the substrate surface is tapered to reduce a bend in a height direction of the second electrode.

10. The chip of claim 9, wherein the bottom surface of the second flow channel forms an obtuse angle with a side wall surface in an area where the second electrode is provided.

11. The chip of claim 8, wherein:

the second flow channel comprises an insulating film tunnel and has a part crossing the first flow channel, the second electrode is provided from an inner wall upper surface of the second flow channel to the substrate surface, and the inner wall upper surface of the second flow channel forms an obtuse angle with a side wall surface in an area where the second electrode is provided.

12. The chip of claim 11, wherein the second flow channel is formed in a trapezoidal shape whose upper side is shorter than its lower side in cross section.

13. The chip of claim 8, wherein the first and second electrodes are provided in proximity to the micropore.

14. A manufacturing method of a semiconductor micro-analysis chip, the method comprising:

performing selective etching of a substrate surface to form a first flow channel engraved in a substrate into which a sample liquid can flow and a reservoir engraved in the substrate to provide an inlet or outlet for the sample liquid;

forming a micropore at a part of the first flow channel, the micropore being configured to have microparticles in the sample liquid pass therethrough;

forming a side wall taper surface in a part of the first flow channel or a part of the reservoir such that a bottom surface of the first flow channel or a bottom surface of the reservoir forms an obtuse angle with a side wall surface thereof; and forming a first electrode in a part of the first flow channel or a part of the reservoir, from the bottom surface of the first flow channel or the reservoir to the substrate surface of the substrate along the side wall taper surface.

15. A semiconductor micro-analysis chip, comprising:

a first flow channel provided at a substrate surface, the first flow channel being engraved in the substrate and being configured to have a sample liquid flow therein;

a second flow channel provided at the substrate surface and having a part close to or crossing the first flow channel, the second flow channel being configured to have the sample liquid or an electrolyte solution flow therein;

a micropore provided at a closest point or a crossing point of the first and second flow channels, the micropore being configured to have microparticles in the sample liquid pass therethrough;

first reservoirs provided at both ends of the first flow channel, the first reservoirs being engraved in the substrate and providing an inlet and outlet for the sample liquid;

second reservoirs provided at both ends of the second flow channel, the second reservoirs being engraved in the substrate and providing an inlet and outlet for the sample liquid or the electrolyte solution;

a first electrode provided from a bottom surface of the first reservoir on a sample liquid inlet side to the substrate surface, wherein a side surface which connects the bottom surface of the first reservoir and the substrate surface is tapered to reduce a bend in a height direction of the first electrode; and a second electrode provided from a bottom surface of the second reservoir on a sample liquid or electrolyte solution inlet side to the substrate surface.

* * * * *